United States Patent [19]
Eiler

[11] Patent Number: 5,089,264
[45] Date of Patent: Feb. 18, 1992

[54] METHOD FOR TREATMENT OF BOVINE RETAINED PLACENTA

[75] Inventor: Hugo Eiler, Knoxville, Tenn.

[73] Assignee: The University of Tennessee Research Corporation, Knoxville, Tenn.

[21] Appl. No.: 515,452

[22] Filed: Apr. 27, 1990

[51] Int. Cl.⁵ .................... A61K 37/54; A61K 37/540
[52] U.S. Cl. .................. 424/94.64; 424/94.65; 424/94.66; 424/94.67
[58] Field of Search ............... 424/94.63, 94.64, 94.65, 424/94.66, 94.67

[56] References Cited

U.S. PATENT DOCUMENTS

| | | | |
|---|---|---|---|
| 3,949,073 | 4/1976 | Daniels et al. | 424/177 |
| 4,061,731 | 12/1977 | Gottlieb | 424/101 |
| 4,094,973 | 6/1978 | Robertson | 424/177 |
| 4,191,751 | 3/1980 | Gottlieb | 424/177 |
| 4,511,653 | 4/1985 | Play et al. | 435/69 |
| 4,621,631 | 11/1986 | Laques et al. | 128/156 |

OTHER PUBLICATIONS

Bierschwal, C. J., Retained Placenta in the Dairy Cow, *The Bovine Proceedings*, No. 12, Apr. 1980, pp. 102–104.
Britt, Jenks S., Management of Retained Placentas in Practice, *The Bovine Proceedings*, No. 12, Apr. 1980, p. 105.
Squire, Allen G., Management of Retained Placenta in Large Southern CA. Dairy Herds, *The Bovine Proceedings*, No. 12, Apr. 1980, p. 106.
Joosten, I. et al., Factors Related to the Etiology of Retained Placenta in Dairy Cattle, *Animal Reproduction Science*, 14, (1987), pp. 251–262.
Joosten, I. et al., Economic and Reproductive Consequences of Retained Placenta in Dairy Cattle, *The Veterinary Record*, (1988) 123, pp. 53–57.

*Primary Examiner*—Douglas W. Robinson
*Assistant Examiner*—Jean C. Witz
*Attorney, Agent, or Firm*—Luedeka, Hodges, Neely & Graham

[57] ABSTRACT

A method and medicament for the treatment of bovine retained placenta membrane. The medicament comprises at least one proteolytic enzyme and in the preferred method, the medicament is administered via at least one of the blood vessels serving the umbilical cord of the host.

12 Claims, No Drawings

METHOD FOR TREATMENT OF BOVINE RETAINED PLACENTA

This invention was made with government support under the HATCH program of the United States Department of Agriculture. The government has certain rights in this invention.

This invention relates to the treatment of retained fetal membranes (RFM) in cows, and particularly to a method and medicament for treating such condition.

The occurrence of retained fetal membranes (RFM) for all calving in the United States is approximately 11%. The average cost of RFM in the dairy cow is estimated to be approximately $200 per cow. This cost is occasioned by reason of reduced milk production, treatment cost, increased culling rate and extended calving interval. Beef cattle are likewise adversely affected by RFM, but to a lesser dollar value.

A specific and effective treatment for this disease in cows is not available. Manual removal of the fetal membranes in contraindicated.

Fetal membranes should be expelled within two to three hours in 80% to 90% of normal calvings. RFM is deemed to be present when expulsion has not been accomplished by 12 hours postpartum. Retention of fetal membranes can be secondary or primary. In secondary retention, membranes remain in the uterus because of atony of the uterus or the existence of a mechanical impediment to membrane expulsion. In primary retention, fetal membranes remain attached to the caruncle. The cause for primary retention is unknown.

Typically, retained fetal membranes are present as a partially visible mass of membranes hanging out of the vagina. A fetid discharge may also accompany RFM. In most severe cases of RFM, acute septic metritis, peritonitis and/or septicemia may develop. These complications result in cow death in 1% to 4% of afflicted cases. Furthermore, cows with RFM are 19 times more likely to contract metritis than animals which do not have RFM. Retained fetal membranes accompanied by any of these complications seriously impair subsequent fertility for a variable length of time. Reproductive parameters which are adversely affected include conception to first service, conception rate, time for uterine regression, calving interval and total number of days open.

The etiology of primary RFM is unknown and there is no satisfactory treatment. General supportive therapy includes the use of antibiotic and uteritonic drugs. As noted, the traditional manual removal of RFM is contraindicated inasmuch as such increases mortality rate, and decreases conception rate at first service.

It is therefore an object of the present invention to provide a novel method for the treatment of RFM. It is another object to provide a medicament that is effective in the treatment of RFM It is another object to provide such a method and/or medicament which is effective in promoting loosening of RFM within about 24 hours from administration of the treatment. It is another object to provide a method and/or medicament for the treatment of RFM wherein such method and/or medicament is specific in function and essentially non-injurious to the cow. It is another object to provide a relatively inexpensive method and/or medicament for the treatment of RFM.

In accordance with the present invention, it has been discovered that the administration of at least one proteolytic enzyme directly to the retained membranes, and particularly via the vessels of the umbilical cord, in a treatment effective amount, will result in loosening of the retained membranes within about 24 hours following administration. A preferred enzyme is collagenase. Dosages are dependent upon the particular enzyme and range between about 1 to about 100,000 units per 3 g of placental tissue. Typical dosages for various enzymes are presented in Table I. Preferably the dosage is kept as small as is effective to loosen the RFM, but higher dosage may be required where the adhesion between the caruncle and cotyledon is more pronounced.

TABLE I

| Enzyme | ENZYME DOSAGES Dose Levels (units/3.0 g tissue) | | |
|---|---|---|---|
| Collagenase | 1,000 | 5,000 | 10,000 |
| Papain | 1.0 | 5.0 | 10.0 |
| Pepsin | 1,000 | 5,000 | 10,000 |
| Trypsin | 10,000 | 50,000 | 100,000 |

It has been found that maternal and fetal connective tissue in the bovine placentome becomes increasingly collagenized up to the time of parturition. At parturition, the maternal cryptal epithelium nearest the carunclar stalk becomes flattened. Binucleate cells develop into reabsorptive, phagocytic, giant polynuclear cells just prior to detachment. With the onset of parturition the imbibed tissues of the placentome become loose. Histological examination of the fetal cotyledons and maternal caruncle tissues sampled at 5 hours postpartum showed degeneration and necrosis of the fetal villi and the epithelium of maternal crypts with the latter filled with debris. The detachment of the terminal portions of the chorionic villi from the maternal crypts play a role in separation of the fetal and maternaplacenta. The present inventors have found that enzymatic hydrolysis of collagen represents a substantial part of the mechanism for the maternal fetal tissues separation.

To be clinically useful, treatment of RFM should be effective within 24 hours of administration to the affected cow. Otherwise, the cervix tends to close partially, thereby preventing a hand to pass through and pull apart loose membranes from the caruncles, if the membranes are not expelled spontaneously as a result of the treatment.

A key component of the present invention is the injection of protease(s) into the retained placenta via the umbilical cord vessels. Injection via the umbilical cord vessels, and particularly the arteries, offer the advantages of (1) localized enzyme effect at the caruncle-cotyledon interphase, sparing interplacentome endometrium, thereby preventing uterine wall digestion and possible uterine rupture, (2) decreased risk of both immunogenicity and systemic reactions, (3) use of relatively small amount of enzyme, as contrasted with systemic administration, and (4) ability to use enzymes that otherwise might adversely affect the cow, such as enzymes and/or combinations of enzymes that may cause blood clotting when injected systemically.

In accordance with the present method, in the administration of the selected enzyme(s), the umbilical cord is retrieved from the uterus and at least one, and preferably the four primary blood vessels serving the umbilical cord are identified and separated as necessary to permit their catherization, the catheter being preferably ligated in place. Once the catheter(s) are in place, a selected dose of protease dissolved in warm normal saline (calcium ions added; e.g., about 10 mg CaCl$_2$ per 100 ml of saline) is injected into each vessel. Preferably, the total dosage is subdivided into aliquots equal in number to the number of isolated blood vessels. Each vessel then receives its proportional share of the total dosage. Injection into a single artery is effective for distribution of the enzyme to all placentomes inasmuch as both arteries of the umbilical cord are joined by a major anastomosis. Injection through umbilical veins is not as efficient as through arteries because of the valve system in the veins that limits backflow of blood plus each of the veins only serves about ½ of the placentomes. During injection, the veins become grossly extended in contrast to the less ballooned arteries.

Expulsion of the placenta is determined by visual inspection of hanging membranes, preferable at least once every 4 hours for the first 24 hours post treatment. When hanging membranes are not observable, a vaginal palpation is given to verify expulsion. Where complete expulsion is not affected within 24 hours of treatment, it has been found that the caruncle-cotyledon adhesion has been lessened to the extent that the placenta can be removed by gentle pulling without tearing it into pieces as has been the experience heretofore during manual removal of the placenta. In such instances, the manual removal after treatment in accordance with the present invention does not adversely affect the uterine wall, hence reduces the adverse affects heretofore noted, of increase of mortality rate and decrease in conception rate at first service.

Collagen forms insoluble fibers that have great tensile strength and are involved in giving structural support to organs and cells and in directing developing Collagen is an important determinant of the 3-tissues dimensional form of the uterus. Types I, III and V are found in the uterine tissue, amnion and chorion and types I, III, IV and V in the placental villi. The amount of collagen found in the mammalian uterus increases rapidly during gestation. Generally, the collagen content of the mammalian uterus increases during pregnancy at a rate slightly less than that of the wet weight increase. This rate of increase in collagen is substantially greater than that observed in the non-uterine tissues undergoing growth, such as the thyroid and liver. Collagen is the most abundant protein in mammals. Its basic structural unit consists of three polypeptide chains. The arrangement and type of the approximate 1000 amino acids residues in the polypeptide chains determine the type of collagens formed. The polypeptide chains are called alpha chains (alpha 1, alpha 2 and alpha 3), the chains aggregating in different combinations to form the triple helices of the various collagen types. Collagen's three principle amino acids are glycine, proline and hydroxyproline.

After parturition the uterus undergoes regression. Drastic reduction in size and a reorganization of tissues is necessary before another pregnancy can be maintained. In the cow, there is a loss of about 8 kg of uterine mass within 30 days following parturition, and about 33% of the loss is collagen. Further loss of tissue due to the degeneration of the smaller arteries occurs with the extensive necrosis of the superficial regions of the endometrial caruncles. Epithelial regeneration over the maternal caruncles is completed by about days 19 and 25 postpartum. The time required for complete uterine involution, which is dependent on collagen breakdown and resorption, is variable: tissue samples of bovine postpartum uteri indicate that involution is complete at 50 days postpartum.

In accordance with the present invention, it has been found that degradation of the collagen of the caruncle-cotyledon interphase results in enhancement of the release of the placenta from the uterine wall, apparently by reason of the degradation of the adhesion of the cotyledons to the caruncles. Further, such degradation has been found to be effectively and efficiently accomplished by the administration of a treatment effective amount of at least one proteolytic enzyme. Administration of the enzyme preferably is made site-specific by means of the preferred injection of the enzyme into the vascular structure of the placenta. Whereas treatment is effective when administered postpartum, following natural birthing, administration of the enzyme following either Caesarean section or dystocia is indicated as a prophylactic measure inasmuch as the blood vessels of the placenta become non-functional postpartum and the distribution of the enzyme is therefore substantially restricted to the placenta, including the interphase between the caruncles and cotyledons and therefore is not detrimental to the cow.

In view of the chosen mode of administration and the limitation of the distribution of the enzyme within the placenta, the present invention provides for the use of a relative wide range of enzymes. Generally, the selected enzyme must be proteolytic and preferably is collagen-specific. However, it has been noted that degradation of collagen in some instances involves not only the initial hydrolysis of the collagen, but often includes the further activity of supplementary enzymatic activity, such as those enzymes that reduce polypeptide fragments to smaller peptides and amino acids. Thus, the present invention contemplates the incorporation in the injected solution of multiple enzymes which may function individually and/or in combination to enhance the release of the placenta. The enzymes of collagenase, papain, pepsin, and trypsin, single or blended, have been demonstrated to affect collagen degradation, hence are indicted to promote release of the placenta. Of these enzymes, papain, pepsin and trypsin are known to promote blood clotting, but in the present invention such adverse effect is circumvented through the use of the postpartum-non-functional vascular system of the placenta as the route of administration. Other proteolytic enzymes include: streptokinase, plasminogen, urokinase, aminopeptidase, carboxypeptidase: A, B, Y, P, chymotrypsin, cathepsin, elastase, leucin aminopeptidase, plasmin, clostripain, and neutral protease. The expense and commercial availability of a particular enzyme partly dictate its use in the present invention. Similarly, the preferred enzyme is compatible with antibiotics such as tetracycline, etc.

Collagenase is a preferred enzyme. Two types of collagenase are known. One is secreted by microorganisms, such as *Vibrio algino lyticus, Achromobaceter iophaous/bacillus polymyxa*, and *Clostridium histolyticum*, and the other is found in mammalian and amphibian tissues. Collagenase does not appear to be lysosomal in origin. No appreciable amount of collagenase is stored in tissue. Products resulting from digestion with bacterial collagenase are different from those seen from digestion with vertebrate collagenase. Vertebrate collagenase produces the first and critical cleavage in the helical body of the collagen molecule. Other enzymes follow and reduce polypeptide fragments to smaller peptides and amino acids. Bacterial collagenase splits each polypeptide chain at more than 200 sites. Bacterial collagenase is also able to release hydroxyproline from uterine collagen and likely is not a single enzyme, but rather it most likely exists in multiple forms. Bacterial collagenase is preferred in the present invention because it is active in digesting placentomes and is commercially available.

Employing in vitro studies, the present inventors have established the proteolytic activity of bacterial collagenase with respect to enhancement of the release of placenta, as measured by the separation of the cotyledon from its associated caruncle. These studies included laboratory analysis of the proteolytic activity of the enzyme, and physical measurement of the separation of the cotyledons from the caruncles. These studies were followed by in vivo study of the effectiveness of the method and medicament.

In in vitro studies, three grams of fresh, minced caruncle, cotyledon, and/or interplacentome endometrium were incubated in normal saline (10 ml), with calcium ions added for various periods of time, e.g. 2,4,6, and 8 hours periods, at 38° C., in a shaker. Incubation pH was adjusted to enzyme maximal activity. Hydrolytic activity of the enzyme was evaluated in the supernatant of the incubated material, after centrifugation, by determination of hydoxyproline (collagen hydrolysis), and total nitrogen (protein content). Hydroxyproline was determined by hydrolyzing the sample in 6N HCl, pH adjusted with KOH, and then saturated with KCl. The sample was then oxidased by chloramine T. After extraction with toluene, Ehrlich's reagent was added and absorbance was read at 560 nm. Total nitrogen was determined by the routine Kjeldahl method (Branstreet, R. B.: The Kjeldahl Method for Organic Nitrogen, Academic Press, N.Y., (1965)). Data representing the results of these studies are presented in Tables II and III and show strong proteolytic activity of the enzyme.

TABLE III

CONCENTRATIONS OF HYDROXYPROLINE AND TOTAL PROTEINS IN THE SUPERNATANT OF PLACENTOME SAMPLES (3.0) GRAMS) INCUBATED FOR 6 HOURS (38° C., pH 7.0) WIth COLLEGANESE

| Collagenase (Units/g Placentome) | No | Hydroxyproline ($\mu$g/ml) | Total Proteins (mg/ml) |
|---|---|---|---|
| 3330 | 30 | 161.4[a] | 40.1[a] |
| 1660 | 30 | 93.6[b] | 27.3[b] |
| 333 | 20 | 12.0[c] | 15.4[c] |
| 166 | 20 | 6.5[c] | 9.8[cd] |
| 83 | 20 | 5.5[c] | 8.8[cd] |
| 42 | 20 | 4.5[c] | 7.7[cd] |
| 0 | 20 | 1.7[c] | 6.0[d] |

[a, b, c, d] with different superscript are statistically significant ($p < 0.05$).

The loosening effects of fetal membranes from caruncle, as a function of time, was examined. These tests involved examination of isolated placentomes by a manometric technique and of whole uteri by a gravity technique. In the manometric technique, each placentome (caruncle and attached cotyledon) was excised from the uterus and weighed. All blood vessels were ligated and the placentome placed in a heated (38° C.) chamber to prevent dehydration. Protease was injected into the most prominent umbilical blood vessel serving the cotyledon. To measure the loosening effects of the protease on the caruncle-cotyledon attachment, using intestinal forceps a 4.0 cm length by 1.0 cm width rubber balloon was inserted lengthwise between the fetal membranes and the caruncle. The balloon was attached to a modified mercury manometer. As the manometer air pump was actuated, the balloon increased in diameter exerting a pulling force between the fetal membranes and caruncle. It was found that at about 40 mm Hg pressure, about 10% C.V., the fetal maternal attachment suddenly released. At this point, the pressure in the balloon was recorded. This simple technique provided consistent results and the ability to detect significant changes in the caruncle-cotyledon attachment, such as the differences in force required to effect release of the attachment between treated and non-treated caruncle-cotyledon units. Employing this technique, it was demonstrated that through the use of proteolytic enzymes, the caruncle-cotyledon attachment is loosened relative to the degree of attachment of untreated carunle-cotyledon units, as shown in Table IV.

TABLE II

QUALITATIVE DESCRIPTION OF PLACENTOME DIGESTION BY DIFFERENT ENZYMES AS FUNCTION OF TIME

| Item Observed | Collagenase (1,000 U) | | | Trypsin (10,000 U) | | | Papain (1.0 U) | | | Pepsin (1,000 U) | | | Control (No Enzyme) | | |
|---|---|---|---|---|---|---|---|---|---|---|---|---|---|---|---|
| | 1 h | 3 h | 6 h | 1 h | 3 h | 6 h | 1 h | 3 h | 6 h | 1 h | 3 h | 6 h | 1 h | 3 h | 6 h |
| LIQUEFACTION: | | | | | | | | | | | | | | | |
| caruncle | + | ++ | +++ | ++ | +++ | +++ | + | +++ | +++ | ++ | ++ | ++ | − | − | − |
| cotyledon | + | +++ | +++ | +++ | +++ | +++ | + | ++ | +++ | − | + | + | − | − | − |
| GELATINOUS SUBSTANCE | − | − | + | + | ++ | +++ | + | ++ | +++ | − | − | − | − | − | − |
| SULFUR ODOR | + | ++ | ++ | − | − | − | − | + | ++ | − | − | − | − | − | − |
| CARUNCLE/ COTYLEDON SEPARATION | + | ++ | +++ | + | +++ | +++ | + | +++ | +++ | + | +++ | +++ | + | + | + |

(−) = none, (+) = minimum, (+++) = maximum. Three grams placentome sections were incubated for 1, 3 and 6 hours (38° C.) in buffer adjusted to enzyme optimal pH. Different concentration of enzymes were used.

TABLE IV

| Condition | No. | Pressure Needed for Caruncle/Cotyledon Separation (m³Hg) | % Change |
|---|---|---|---|
| CONTROLS | | | |
| NOT PERFUSED WITH BLOOD | 20 | 37.9 ± 2.5$^a$ | — |
| PERFUSED WITH BLOOD | 9 | 31.1 ± 3.1$^a$ | — |
| TREATED | | | |
| PERFUSED WITH BLOOD PLUS COLLAGENASE | | | |
| 16 units/ml | 9 | 13.0 ± 1.9$^b$ | 41.8 |
| 116 units/ml | 9 | 15.7 ± 2.5$^b$ | 50.4 |

$^{a,\ b}$Different superscripts indicates statistically significant (P < 0.05) difference. Notice collagenase decreased pressure needed to separate cotyledon from caruncle.

Placenta separation by gravity was employed as a measure of the effectiveness of enzymatic dosage on the total number of placentomes in the whole uterus. In this technique, the selected protease is dissolved in 1,000 cc normal saline (calcium ions added), immediately before use. Each umbilical blood vessel, four total, was injected with 250 cc of the solution and ligated. The uterus was placed in a sealed and moisturized (saline) plastic bag, and incubated at 38° C. for 12 hours. At the end of the 12 hour incubation, the uterus was suspended by the umbilical cord (without grasping the uterus), thereby causing the weight of the uterus (about 5 kg) to pull down and separate the fetal membranes from the caruncles by gravity. The time required for separation was recorded and compared to a saline injected control. Employing collagenase as the enzyme, the treated uterus commonly separates in less than one minute after suspension, whereas control uteri do not separate for 10 minutes or longer. In certain instances, the enzymatic activity was such that attempts to lift the uterus by the umbilical cord resulted in separation of the caruncle-cotyledon units with minimal effort and before the uterus could be suspended. Data showing the times for separation of the cotyledons from their associated caruncles for successfully suspended uteri are given in Table V.

TABLE V

| Enzyme | No. | Number of uteri separated from cotyledon at | | | |
|---|---|---|---|---|---|
| | | 1.0 Min. | 10 Min. | 1.0 h | 2.0 h |
| CONTROL | 6 | 0/6 | 0/6 | 0/6 | 0/6 |
| COLLAGENASE (200,000 units) | 6 | 6/6 | — | — | — |
| PAPAIN (16,000 units) | 3 | 2/3 | 1/3 | — | — |
| PEPSIN (3,000,000 units) | 1 | 0/1 | 1/1 | — | — |
| TRYPSIN (7,000,000 units) | 1 | 1/1 | — | — | — |

(0/6) = none of six uteri. Each protease was dissolved in 1000 ml saline at enzyme optimal pH and uteri incubated at 38° C. for 12 hours. At 12 hours a gravity testing was performed.

The effectiveness and efficiency of the present method and medicament were tested in vivo employing the aforedescribed techniques involving, preparation of a medicament comprising at least one proteolytic enzyme in solution, and injection of the same into the umbilical blood vessels of the cow, and observation of the expulsion of the placenta. Table VI presents the data representing the results of these in vivo tests and employing collagenase as the enzyme. In 85% of the instances, the placenta was expulsed within 24 hours following treatment. There were no clinical signs, blood chemistry nor hematological indications of side effects associated with these treatments. Specifically, there was no noted blood clotting effects.

TABLE VI

| TREATMENT | 8–24 hours | 2–4 days | 5–7 days | 8–10 days |
|---|---|---|---|---|
| COLLAGENASE IN SALINE | 17/20 (85%) | 0/20 (0.0%) | 2/20 (10%) | 1/20 (5%) |
| SALINE (1000 ml) | 0/8 (0.0%) | 0/8 (0.0%) | 3/8 (37.5%) | 5/8 (62.5%) |

(17/20) = Seventeen of 20 cows.
(%) = Percentage of cows that either detached and/or expelled a placenta. Dose of collagenase was either 200,000 units (11 cows) or 400,000 units (9 cows). 35% cows received collagenase injection into 2 of 4 blood vessels, 30% in 3, and 35% in 4. Eight cows suffered from spontaneous retained placenta and 12 from experimentally induced retained placenta; 7 and 10 cows respectively responded within 24 hours of collegenase injections.

The cost of treatment employing the present method and medicament ranges between about $1.00 and $15.00 per cow for the medication. The quantity of enzyme required is small relative to systemic administration which requires about 2.2 million units collagenase per cow and introduces a greater possibility of immunoreactivity. However, if preferred, systemic administration of collagenase may be employed, such as in those instances where it is not possible to gain access to the umbilical vessels or for other reasons. Such routes of administration require greater attention to the enzyme or combination of enzymes employed to avoid adverse side effects, particularly blood clotting.

As employed herein, the following definitions of "unit" apply:

COLLAGENASE: One unit liberates peptides from collagen (C 9879) (from Sigma Company) equivalent in ninhydrin color to 1.0 micromole of leucine in 5 hr. at pH 7.4 at 37° C. in the presence of calcium ions.

PAPAIN: One unit will hydrolyze 1.0 micromole of BAEE per min. at pH 6.2 at 25° C.

PEPSIN One unit will produce a delta A280 of 0.001 per min. at pH 2.0 at 37° C., measured as TCA-soluble products using hemoglobin as substrate.

TRYPSIN One BAEE unit=delta A253 of 0.001 per min. with BAEE as substrate at pH 7.6 at 25° C.

Whereas there has been described the administration of a single enzyme, it is to be recognized that the administered solution may include more than one enzyme and/or may include other components such as an antibiotic. Also, whereas injection via the blood vessels serving the umbilical cord is preferred, it is noted that administration may be by topical means, such as a sponge or the like which bears the solution in question and which is inserted into the placentome in the vicinity of the caruncle-cotyledon interphase. Other combinations of enzymes and/or pharmaceuticals and/or modes of administration will be recognized by one skilled in the art, given the present disclosure.

Whereas the invention has been described in specific terms and with respect to specific examples, it is not intended to limit the invention other than as set forth in the claims appended hereto.

What is claimed:

1. A method for the treatment of a host bovine afflicted with retained placenta membrane comprising the administration to the host of an effective amount of at least one proteolytic enzyme selected from the group comprising collagenase, papain, pepsin and trypsin.

2. The method of claim 1 wherein said enzyme comprises a combination of effective enzymes.

3. The method of claim 1 wherein said enzyme comprises collagenase.

4. The method of claim 3 wherein said collagenase is derived from microorganisms.

5. The method of claim 4 wherein said microorganism is selected from the group comprising *Vibrio alginolyticus, Achromobaceter iophagus/bacillum polymyxa, and Clostridium histolyticum*.

6. The method of claim 1 wherein said enzyme is in solution and administered via injection into at least one of the blood vessels serving the umbilical cord.

7. The method of claim 6 wherein said one of the blood vessels is an artery.

8. The method of claim 1 wherein said effective amount of said enzyme is between about 1 and about 100,000 units.

9. The method of claim 1 wherein said effective amount of said enzyme is sufficient to effect substantial loosening of the attachment of cotyledons in said placenta from their associated caruncles within about 24 hours following injection of said enzyme.

10. A method for the treatment of bovine retained placenta membrane comprising the steps of identification of at least one of the blood vessels serving the umbilical cord of a host bovine, and injection into said blood vessel of an effective amount of a proteolytic enzyme selected from the group comprising collagenase, papain, pepsin, and trypsin.

11. The method of claim 10 wherein said method is performed postpartum.

12. The method of claim 10 wherein said identification and injection steps are carried out contemporaneously with dystocia or a Caesarean section conducted on said host.

* * * * *

UNITED STATES PATENT AND TRADEMARK OFFICE
CERTIFICATE OF CORRECTION

PATENT NO. : 5,089,264
DATED : February 18, 1992
INVENTOR(S) : Hugo Eiler

It is certified that error appears in the above-identified patent and that said Letters Patent is hereby corrected as shown below:

Column 1, line 56

After "RFM", insert --.--.

Column 3, line 34

After "developing", insert --tissues.--.

Column 3, line 35

After "3-", delete --tissues--.

Column 4, lines 57-58

After "Achromobaceter", delete "iophaous" and insert --iophagus-- therefor.

Column 7, Table V

Before "200,000 units" insert --(--.

Column 8, line 53

After "PEPSIN", insert --:--.

UNITED STATES PATENT AND TRADEMARK OFFICE
CERTIFICATE OF CORRECTION

PATENT NO. : 5,089,264
DATED : February 18, 1992
INVENTOR(S) : Hugo Eiler

It is certified that error appears in the above-indentified patent and that said Letters Patent is hereby corrected as shown below:

Column 8, line 56

After "TRYPSIN", insert —:—.

Signed and Sealed this

Thirty-first Day of August, 1993

Attest:

BRUCE LEHMAN

Attesting Officer

Commissioner of Patents and Trademarks